United States Patent
Boyer, III et al.

(10) Patent No.: US 6,191,055 B1
(45) Date of Patent: Feb. 20, 2001

(54) OIL-TOLERANT REINFORCEMENT STRIP

(75) Inventors: Charles E. Boyer, III, Oakdale; Robert J. Kinney, Woodbury; Ramsis Gobran, Roseville; Ruben E. Velasquez Urey, St. Paul; Roland R. Midgley, Minneapolis, all of MN (US)

(73) Assignee: 3M Innovative Properties Company, St. Paul, MN (US)

( * ) Notice: Under 35 U.S.C. 154(b), the term of this patent shall be extended for 0 days.

(21) Appl. No.: 09/181,531

(22) Filed: Oct. 28, 1998

Related U.S. Application Data

(62) Division of application No. 08/769,064, filed on Dec. 18, 1996, now Pat. No. 5,885,269.

(51) Int. Cl.$^7$ ................ A61F 13/58; B32B 27/04
(52) U.S. Cl. ................ 442/80; 428/99; 428/304.4; 428/315.5; 428/355; 604/38.1; 604/386; 604/389; 604/390
(58) Field of Search ................ 604/385.1, 386, 604/389, 390; 428/99, 304.4, 315.5, 355; 442/80

(56) References Cited

U.S. PATENT DOCUMENTS

| | | |
|---|---|---|
| 3,991,002 | 11/1976 | Sadlo . |
| 4,237,889 | 12/1980 | Gobran ................ 128/287 |
| 4,539,256 | 9/1985 | Shipman ................ 428/315.5 |
| 4,861,635 | 8/1989 | Carpenter et al. . |
| 4,902,553 | 2/1990 | Hwang et al. ................ 428/156 |
| 5,019,071 | 5/1991 | Bany et al. ................ 604/389 |
| 5,106,383 | 4/1992 | Mulder et al. ................ 604/389 |
| 5,112,889 | 5/1992 | Miller et al. ................ 524/77 |
| 5,264,281 | 11/1993 | Arakawa et al. ................ 428/354 |
| 5,308,695 | 5/1994 | Arakawa et al. ................ 428/354 |
| 5,468,237 | 11/1995 | Miller et al. . |
| 5,562,983 | 10/1996 | Kono et al. . |
| 5,885,269 | 3/1999 | Boyer, III et al. . |

FOREIGN PATENT DOCUMENTS

| | | | |
|---|---|---|---|
| 663894 | 4/1994 | (AU) . | |
| 677912 | 11/1995 | (AU) . | |
| 2221172 | 3/1994 | (CA) . | |
| 0 291 984 | 11/1988 | (EP) | ................ A41B/13/02 |
| 0 306 232 | 3/1989 | (EP) | ................ C09J/3/14 |
| 0 375 862 B1 | 8/1994 | (EP) . | |
| 0 661 959 B1 | 7/1995 | (EP) . | |
| 106812 | 8/1993 | (IL) . | |
| 54-145740 | 11/1979 | (JP) | ................ C09J/7/02 |
| 58-149303 | 9/1983 | (JP) | ................ A41B/13/02 |
| 57-165978 | 5/1984 | (JP) | ................ A41B/13/02 |
| 59-228008 | 12/1984 | (JP) | ................ A41D/13/08 |
| 62-282003 | 12/1987 | (JP) | ................ A41B/13/02 |
| 63-161035 | 7/1988 | (JP) | ................ C08J/9/00 |
| 63-309605 | 12/1988 | (JP) | ................ A41B/13/02 |
| 1-162804 | 6/1989 | (JP) | ................ A41B/13/02 |
| 9305407 | 7/1994 | (MX) . | |
| 936070 | 8/1993 | (SA) . | |
| WO 92/08763 | 5/1992 | (WO) | ................ A61F/13/60 |
| WO 94/06387 | 3/1994 | (WO) . | |

*Primary Examiner*—Terrel Morris
*Assistant Examiner*—Arti R. Singh
(74) *Attorney, Agent, or Firm*—Gary L. Griswold; Robert W. Sprague; William J. Bond

(57) ABSTRACT

A diaper construction is provided with an external porous reinforcement strip at the front part of the outside of the diaper, which strip provides reinforcement against an adhesive fastening tab and provides an oil contamination tolerant adhesion surface.

8 Claims, 1 Drawing Sheet

OIL-TOLERANT REINFORCEMENT STRIP

This is a division of application Ser. No. 08/769,064 filed Dec. 18, 1996 now U.S. Pat. No. 5,885,269 Mar. 23, 1999.

BACKGROUND AND FIELD OF THE INVENTION

The present invention relates to improved disposable articles such as diapers, incontinent products, disposable garments, feminine hygiene products, and the like.

Disposable baby diapers are often used in conjunction with powders or oils applied by the parent onto the baby. Quite often, the powder or oil contaminates the outer backsheet portion of the diaper. Typically, the powder or oil is transferred to the diaper backsheet by the parent's hands or from the baby. A persistent problem with such powder and oil contamination is that conventional adhesive tab closures used with diapers are adhered onto the outer backsheet portion of the diaper and do not adequately adhere to surfaces contaminated with talc or particularly oil.

U.S. Pat. No. 4,163,077 proposes a diaper closure system wherein the adhesive used on the fastening tab is a particular blend of a synthetic block copolymer and a blend of solid and liquid polyterpene type tackifiers. This adhesive provides a limited ability to adhere to talc or powder contaminated diaper surfaces, such as polyethylene backsheets typically employed in commercial diaper constructions. However, this adhesive composition does not address the problems of adhering to an oil-contaminated diaper substrate.

The problem of adhering to oil-contaminated surfaces with conventional pressure-sensitive adhesives is addressed in U.S. Pat. No. 3,991,002, which describes a method for improving the adhesion of normal pressure-sensitive adhesive tapes to oily or greasy substrates by treating the oil-contaminated substrate with a primer. This primer comprises a rubbery phase of a A-B-A triblock copolymer, such as a styrene-butadiene or styrene-isoprene block copolymer, and a resin phase comprised of a resin compatible with the conjugated diene portion of the block copolymer and a resin compatible with the monovinyl aromatic hydrocarbon portion of the block copolymer (i.e., styrene). These components are placed in a solution, then applied as an aerosol to render the oil-contaminated surface stable for subsequent adhesion. This patent states that the conventional approach to adhering to oil-contaminated surfaces is a complicated and time-consuming clean-up procedure. However, the primer solution proposed in this patent is still impractical for most consumer applications and particularly in a diaper being applied to a baby.

The present invention is addressed at solving the problems identified above. Particularly, the invention is directed at providing a diaper construction provided with a reinforced tape adhesion zone that has the property of oil-contamination tolerance.

BRIEF DESCRIPTION OF THE INVENTION

The present invention provides a disposable garment, generally a diaper, comprising an adhesive fastening tab permanently adhered to one corner of the garment at first end of the tab. A second free end of the adhesive fastening tab is provided to adhere to a reinforced outer surface of the garment to effect closure of the garment by connecting the first-mentioned corner to the reinforced surface by the two adhered ends of the fastening tab. The reinforcement is provided by a reinforcing film or web layer bonded to a thin outer film or web layer of the garment. The reinforcing layer is comprised of a porous film or web wherein the pores preferably contain at least a minor proportion of an incompatible oil or liquid polymer, the porous reinforcement layer providing oil-contamination tolerance, as well as reinforcing the thin outer film against tearing by the removal of the free end of the adhesive fastening tab.

DETAILED DESCRIPTION OF THE INVENTION

Figure 1:
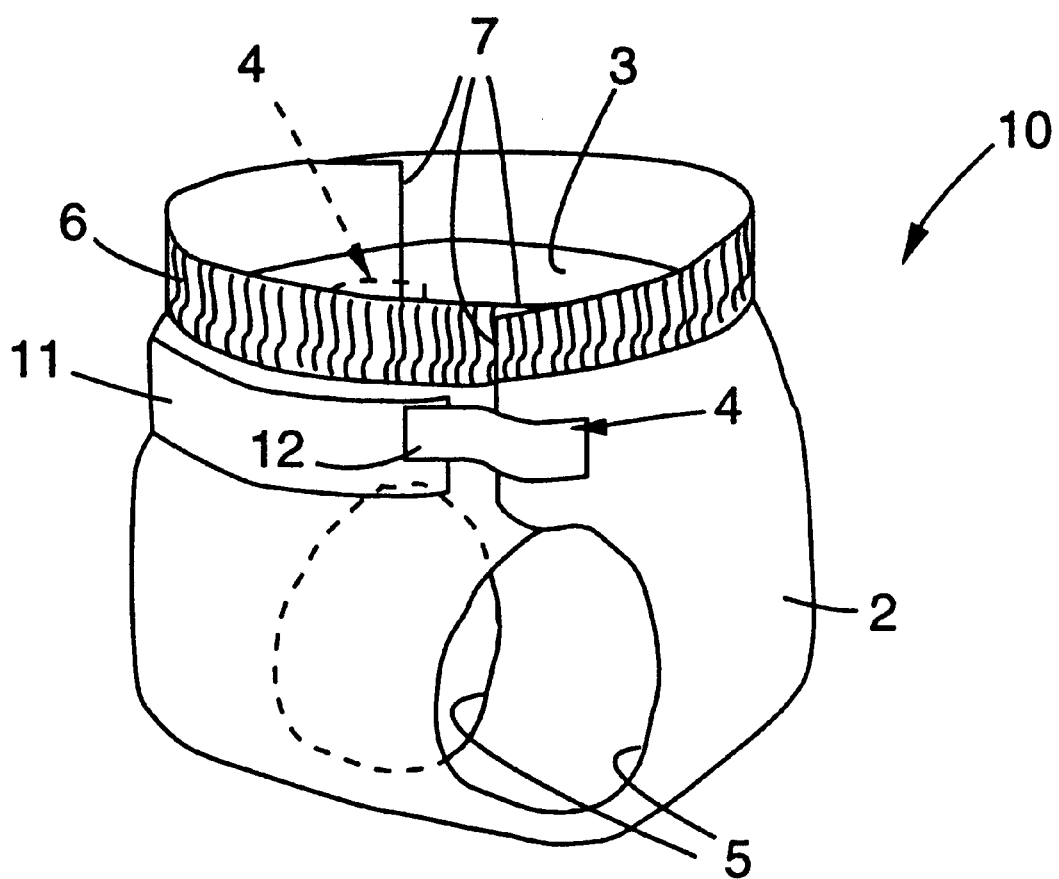
FIG. 1 represents a conventional diaper construction using the invention microporous reinforcement layer as it would look when placed on a wearer.

The invention oil-contamination tolerant adhesive closure system will be described with reference to a conventional baby diaper, however, such a closure system could be used in other applications using the adhesive fastening tabs, such as adult incontinent garments, disposable medical gowns, caps, packaging systems, feminine hygiene articles, and the like.

A conventional diaper construction is depicted in FIG. 1. The diaper 10 is provided with a thin liquid-impermeable outer backsheet 2 and a liquid-permeable inner cover sheet 3. Between the backsheet 2 and inner coversheet 3 is an absorbent core (not shown). Adhesive fastening tabs 4 are provided at two laterally opposed side edge regions 7 at a first end of the diaper. At a second end of the diaper on the backsheet 2 is provided a porous reinforcement layer 11 of the invention. This porous reinforcement layer 11 is permanently bonded to the outside face of the thin diaper backsheet 2 providing a surface to which the free ends 12 of the fastening tab 4 can be adhered. The porous reinforcement layer is likewise located adjacent an edge region 7 so that when the free end 12 of the fastening tab 4 is adhered to the porous reinforcing layer, two edge regions 7 will overlap to effect closure of the diaper undergarment. The porous reinforcement layer then exhibits the ability to provide a suitable surface for adhering a fastening tab free end 12 under normal use conditions, and when the reinforcement layer 11 is contaminated with oil. When the free end 12 of the fastening tab 4 is attached to the porous reinforcement layer 11, there is formed a leg opening 5, which is typically provided with elastic means to form a sealing engagement with the wearer's legs. The diaper may also be elasticated around the waist portion to further provide sealing engagement with the wearer by elasticated portions 6. Prior to use, the adhesive surface on the free end 12 of the adhesive fastening tab 4 is protected from contamination by a release-coated paper or a release-coated tape, which can be provided on the corners 7 of the inner top sheet 3. The backsheet 2 is typically a thin polyethylene film, while the top sheet 3 would typically be a nonwoven such as a spunbond polypropylene. The porous reinforcement layer 11 is attached to the backsheet film by conventional means, which would include the use of hot-melt adhesives.

The reinforcement layer 11 can be a single strip or multiple strips (e.g., one for each fastening tab free end 12). The strip(s) should be provided so that they cover the likely areas where the fastening tab free end 12 would be adhered in normal use.

Oil-contamination tolerance is provided by a porous reinforcement layer having an affinity to oil, but providing a structurally coherent surface. A coherent surface is one that will not delaminate or lose fibers (for a web) when the adhesive tab free end 12 is removed therefrom. Such a porous layer is generally characterized as one having an effective pore size of 20 microns or less, and is preferably a microporous film or web having an effective pore size of 10 microns or less, preferably 1 micron or less. Preferably, the pores will be interconnected. However, some oil tolerance can be provided by layers with unconnected pores such as films with a large number of punched small holes or a microporous film formed with a large number of unconnected small pores.

The porous reinforcement layer 11 may be a microporous film or coherent nonwoven web (one having an effective pore size of about 10 microns or less, preferably less than 1 micron) and is preferably a film such as is disclosed in U.S. Pat. Nos. 4,902,553, 4,539,256, 4,609,584, 4,726,989 or 4,824,719. The material described in these patents comprises a microporous film formed by dissolving a crystallizable polymeric material in a liquid additive at a temperature above the melt temperature of the polymeric material and forming this melt into a film, such as by extrusion. The homogeneous solution is then permitted to cool at a rate suitable to cause the crystallizable polymer to crystallize into a distinct interconnected phase, the polymer being incompatible with the additive at ambient or use conditions. The phase-distinct film material is then uniaxially or multiaxially orientated, creating a film with micropores, which pores contain the now phase-distinct liquid additive. The liquid additive is preferably one which exhibits plasticizing properties or affinity to the adhesive on the free end of the fastening tab. Potential additive materials include saturated hydrocarbons such as mineral oil, glycerin, petroleum jelly, low molecular weight polyethylene, polyethylene oxide, polypropylene oxide, polytetramethylene oxide, soft carbowax, plasticizing oils, and the like. Preferred additive materials are plasticizing oils, with mineral oil being particularly preferred because of its relatively low cost and excellent film-forming properties. The crystallizable polymeric material is preferably olefinic, such as polyolefins, or condensation polymers such as polyesters or polyamides. Most preferred are polyolefins such as crystalline isotactic polypropylene, polyethylene, polybutylene, polyethylpentene, copolymers, block polymers and modified versions thereof.

The additive liquid can be used in an amount ranging from about 5 to 80 percent by weight of the formed film, preferably 5 to 50 percent, and most preferably 10 to 30 percent.

Discussions of crystallizable polymers and phase-separating additives are also found in U.S. Pat. No. 4,247,498 and U.S. Pat. No. 4,100,238. For example, for isotactic polypropylene, these patents describe, the use of phase-separable additives such as poly-1-butene, polyethylene wax, low molecular weight polyethylene, alcohols, aldehydes, amines, esters such as methylene benzoate, ethers such as diphenylether, hydrocarbons such as trans-stilbene or ketones.

Nucleating agents such as those described in U.S. Pat. Nos. 4,824,718 and 4,726,989 can also be used to produce uniform crystallization of the polymeric material upon cooling. These nucleating agents preferably are at least a primary agent, generally an organic acid or derivative, which dissolves in the liquid additive at a temperature at least more than 10° C. above the crystalline transition temperature of the thermoplastic polymer, and which is used in amounts from 0.05 to 5 percent by weight of the system, and optionally a secondary inert nucleating agent, which is employed in approximately the same concentration. The secondary inert nucleating agent normally comprises an inorganic particulate material such as talc, titanium dioxide, calcium carbonate, magnesium carbonate, barium carbonate, magnesium sulfide, barium sulfide, and the like. Suitable organic acids include mono- or polyacids, e.g. carboxylic acids, sulfonic acids, phosphonic acids, and solid organic alcohols such as dibenzylidene sorbitol. The preferred organic acids include adipic acid and succinic acid, and a preferred secondary nucleating agent is talc.

Following precipitation of the thermoplastic crystallizable polymer, the film can be used unoriented or preferably orientated with a stretch ratio, in at least one direction, of 0 to 3, preferably from 1.5 to 2.5. When the film is not oriented, the liquid additive is preferably washed from the film.

Generally, the thickness of the microporous reinforcement sheet is from 5 to 250 microns, preferably from 30 to 200 microns. Comparatively thinner films are preferred in terms of cost and increased moisture vapor permeability where employed for this additional purpose. However, too thin a film may be inadequate in providing an adequate level of reinforcement to prevent the diaper backsheet from tearing. Thicker films provide improved tensile performance and reinforcement against more aggressive adhesives.

Moisture vapor permeability for the, e.g., diaper can be provided by providing holes in the diaper backsheet material 2 behind a microporous reinforcement layer 11. Generally, significant amounts of moisture vapor permeability can be provided even where the holes are quite small, such as pinholes, provided they are provided over a significant portion (e.g., greater than 2 percent open area, preferably greater than 5 percent) of the backsheet film covered by the microporous reinforcement layer. Porous, liquid-permeable (an effective pore size of greater than 1 micron) porous reinforcement layers can also be used in this arrangement, however, are not preferred as they can result in wetting of the wearer's garments.

Alternative porous reinforcement layers include microporous films, without liquid additive, films rendered porous by mechanical means or highly consolidated nonwovens. The microporous films are typically rendered porous by blending in solid particulates, incompatible with the film forming polymer, and then orienting the particulate containing film to create pores. Examples of suitable particulates include calcium carbonate, magnesium carbonate, calcium sulfate, and barium sulfate. The particulates can be present in amounts ranging from about 5 to 80 weight percent, preferably 40 to 70 weight percent of the film. The particle size range can be from about 0.1 to 250 micrometers. At low particle loading levels (e.g., around 5–20 weight percent) the films do not have the preferred levels of porosity and connected pore structure desirable for higher levels of oil-contamination tolerance. Other suitable particulate fillers include talc, clay, silica, diatomaceous earth, alumina, mica, glass powder, asbestos powder, zeolites, zinc oxide, magnesium oxide or organic fillers such as polysiloxanes, or other incompatible polymers or starch or cellulose powder, such as cellulose acetate, provided that the softening point is higher than that of the film forming polymer.

It is also possible to produce non-liquid additive-containing microporous films (porous films which do not contain liquid additive) by removing the liquid additive from the liquid additive-containing porous films with a suitable solvent selective to the liquid additive. Various other known methods for producing microporous films or webs, such as cold stretching of crystalline film forming polymers, are also suitable for forming non-liquid additive containing microporous films.

The pressure-sensitive adhesive on the free end of the fastening tab is preferably a tackified elastomer where the elastomer is an A-B type block copolymer, wherein the A blocks and the B blocks are configured in linear, radial, or star configurations. The A block is mono alkenyl arene, preferably polystyrene, having a molecular weight between 4,000 and 50,000, preferably between 7,000 and 30,000. The A block content is preferably about 10 to 50 percent, more preferably between 10 and 30 percent. Other suitable A blocks may be formed from alpha methyl styrene, t-butyl styrene and other ring alkylated styrenes, as well as mixtures thereof. The B block is an elastomeric conjugated diene, having an average molecular weight from about 5,000 to about 500,000, preferably from about 50,000 to about 200,000. The elastomer preferably comprises at least 15 weight percent, more preferably 25 weight percent, of either block copolymers having B end blocks, such as A-B diblock copolymers, or pure B elastomer, most preferred are A-B block copolymers having B end blocks. The presence of these B block terminated elastomers is preferred in that pressure-sensitive adhesives employing elastomers containing these B block terminated species generally display higher levels of tack to the liquid additive-containing (particularly where the liquid additive is compatible with the elastomeric B block) microporous reinforcement film (both when contaminated with oil and not contaminated with oil), and generally relatively lower levels of tack to the non-liquid additive-containing porous polyethylene films. The non-liquid additive-containing porous films often displayed non-functionally high levels of adhesion (e.g., 135 degree peel values in excess of 1,200 gm/in) to pressure-sensitive adhesives with predominately all A block terminated elastomer species. Further, block copolymers having predominately A block end blocks provide adhesives which have a tendency to lose substantially all adhesive properties when in prolonged contact with the liquid additive-containing microporous film, particularly where the liquid additive is compatible with the B block, such as a mineral oil liquid additive.

The tackifying components for the elastomer-based adhesives generally comprise solid tackifying resin used alone or in combination with a liquid tackifying resin and/or a liquid plasticizer. Preferably, the tackifying resin is selected from the group of resins at least partially compatible with the diene B portion of the elastomeric polymer or block copolymer. Such tackifying resins include those aliphatic hydrocarbon resins made from the polymerization of a feed stream consisting mainly of unsaturated species containing 4 to 6 carbon atoms; rosin esters and rosin acids; mixed aliphatic/aromatic tackifying resins; polyterpene tackifers; and hydrogenated tackifying resins. The hydrogenated resins can include resins made from the polymerization and subsequent hydrogenation of a feed stock consisting mainly of dicyclopentadiene; resins produced from the polymerization and subsequent hydrogenization of pure aromatic feed stocks, such as styrene; resins produced from the polymerization and subsequent hydrogenation of an unsaturated aromatic feed stream, wherein the feed stream consists mainly of species containing 7 to 10 carbon atoms; hydrogenated polyterpene resins; and hydrogenated aliphatic and/or aliphatic/aromatic resins. Preferred tackifying resins include the aliphatic hydrocarbon resins and the hydrogenated resins. Although not preferred, generally, a relatively minor portion of the tackifying resin can include resins compatible with the A block, when present, generally termed endblock reinforcing resins. Generally, these endblock resins are formed from aromatic species.

Suitable liquid plasticizers for use in the fastening tab adhesive composition include naphthenic oils, paraffinic oils, aromatic oils and mineral oils.

Generally, higher composite glass transition temperature adhesives (e.g., above 250 Kelvin) show a better ability to adhere to the liquid additive-containing microporous films, both uncontaminated and contaminated with oil in amounts of up to 0.1 to 0.2 milligrams per square centimeter.

The tackifing portion of the pressure-sensitive adhesive generally comprises from 20 to 300 parts per 100 parts of the elastomeric phase. Preferably, this is predominantly solid tackifier, however, from 0 to 20 weight percent, preferably 0 to 10 weight percent for adhesion to polyethylene surfaces, of the adhesive can be liquid tackifier and/or plasticizer.

Other conventional pressure-sensitive adhesives can be used with the preferred liquid additive-containing porous films or non-liquid additive-containing porous films such as acrylate-based adhesives or adhesives based on other diene or non-diene elastomers or natural rubber.

The closure adhesive fastening tabs, when adhered to the reinforcement layer(s) or film(s), preferably have 135° peel adhesion of less than about 1000 grams per inch, more preferably less than about 800 grams per inch. At adhesions levels above this, the tape is difficult to remove by the end user and risks tearing, e.g., the diaper. Generally, the minimum acceptable 135° peel is approximately 50 grams per inch, and preferably greater than 80 grams per inch.

The liquid additive-containing film is preferred in that the initial adhesion to the non-oil-contaminated reinforcement surface is generally more comparable (and less likely to be excessively high) to the initial adhesion to the oil-contaminated reinforcement surface with a broad range of the above-described pressure-sensitive adhesives, providing a closure with more consistent performance characteristics. Without wishing to be bound by theory, it is believed that the liquid additive-containing reinforcement film system functions by the liquid additive moderating the adhesion levels of the adhesive when the reinforcement strip is not contaminated with oil, while also rapidly removing surface oil from the surface when contaminated.

The porous reinforcement layer has a generally opaque appearance caused by the pore structure. Certain hot-melt adhesives used to apply microporous film can cause the film to become transparent or translucent. Consequently, with these adhesives, it is preferred that the reinforcement layer or film be applied with a full coating of the adhesive for uniform appearance purposes. Certain fastening tab adhesives will also have a tendency to clarify a porous layer or film, which would provide an indication of a suitable location to re-apply the tape tab after opening.

The following examples are the currently contemplated preferred modes for carrying out the invention and should not be considered as limiting thereof unless otherwise indicated in the examples.

EXAMPLES

The following tests were used to evaluate the porous reinforcement film.
135 Degree Peel Adhesion
This test is a modified version of PSTC-5. The test was carried out at constant temperature and humidity (21° C. and 50% relative humidity) using a constant rate Instron™ tensile tester. The film sample to be tested was securely adhered to a 2 in×5 in (5.1 cm×12.7 cm) steel panel using a double-coated adhesive tape. Within 10–60 minutes after securing the film sample to the steel panel a 1 in (2.54 cm) wide strip of test tape was then placed adhesive side down onto the film substrate and was rolled down onto the film substrate using two passes of a 4.5 lb (2000 gm) hard rubber roller. The peel rate was 12 inches (30.5 cm) per minute. The force required to remove the fastening tape from the test substrate is reported in the Tables in grams/inch. Reported values are averages of at least two tests.

Shear Adhesion

The shear adhesion was measured by determining the length of time it took for a 1 in×1 in (2.5 cm×2.5 cm) sample of test tape to shear off of a film test substrate under a 1 kilogram load. A 2 in×6 in (5.1 cm×15.2 cm) piece of the film substrate was laminated to a 2 in×6 in (5.1 cm×15.2 cm) piece of reinforcing tape (3M Y-9377) in order to enhance the stiffness of the substrate. On the side opposite the reinforcing tape, a 1 in×2 in (2.5 cm×5.1 cm) area of the test tape was rolled down onto the film substrate using two passes of a 4.5 lb (2000 gm) hard rubber roller. The overlap area between the test tape and the film substrate was 1 in×1 in (2.5 cm×2.5 cm). The laminated substrate and the test tape were hung vertically in a 40° C. oven for 15 minutes after which a 1 kilogram weight was hung from the test tape, generating a shear load at a 180° angle. The time that it took in minutes for the weight to drop was recorded as a measure of the shear adhesion. Reported values are averages of 5 tests.

Oil-Contamination Test—135 Peel Adhesion from Loose Film and Oil-Contaminated Film Test panels consisted of 2 in×5 in (5.1 cm×12.7 cm) clean steel panels which have had a strip of 0.75 in (1.9 cm) double-coated adhesive affixed along each 2 in (5.1 cm) cross-direction edge. A sheet of the film test substrate was laid down loosely over the test panel so that it was flat without any wrinkles. The cross-direction of the film substrate was parallel to the long dimension of the test panel. The film was rolled down firmly onto the double-coated adhesive and any excess film that extended beyond the edge of the test panel was trimmed away.

The film substrate side of the test panel was contaminated for testing by uniform spray application of a known amount of baby oil onto the panels. The amount of oil deposited was determined by weighing a set of panels before and after spraying and was generally approximately 0.12 mg/cm$^2$. Each sprayed panel was tested within 2 to 4 minutes of completion of oil spraying. Additional panels for comparison were prepared for testing as described above, but were not oil sprayed.

Each strip of test tape measured 1 in×2.5 in (2.5 cm×6.5 cm) with a paper leader measuring 1 in×8 in (2.5 cm×20.3 cm) adhered to the final 0.25 in (0.6 cm) of the tape. This tape assembly was laid with its long dimension parallel to the long dimension of the panel so that the tape was about equidistant from each cross-direction edge of the panel and centered between each longitudinal side edge. No additional pressure was exerted in laying down the tape. The tape was immediately rolled down at 12 inches (30.5 cm) per minute with a single pass of a 100 gm rubber roller and was tested within 15 seconds of completion of rolldown.

An Instron™ tensile tester was used for peel testing the samples. The samples were tested at an angle of 135 degrees throughout the peel at a constant crosshead speed of 12 inches (30.5 cm) per minute. The average peel of each test specimen is reported in the Tables in grams/inch as a measure of the peel adhesion value. The reported values are an average of four tests. The minimum acceptable peel adhesion value for this test is about 30 N/m (about 80 gm/in) for the oil-contaminated films, (i.e., with an oil-contamination level of about 0.12 mg/cm$^2$). Using the same test procedure, tape peeled from a non-contaminated surface should have a minimum peel adhesion value of about 40 N/m about 100 gm/in). The results were reported in gm/in.

In the examples, the pressure-sensitive adhesives for fastening tapes 1–9 were formulated from the following materials.

Kraton™ 1107 is a polystyrene-polyisoprene linear block copolymer available from Shell Chemical Co., having approximately 14–18% diblock and 80–85% triblock, a styrene content of approximately 14%, and a midblock Tg of about 215 Kelvin.

Kraton™ 1111 is a polystyrene-polyisoprene linear block copolymer available from Shell Chemical Co., having approximately 14–18% diblock and 80–85% triblock, a styrene content of approximately 22%, and a midblock Tg of about 215 Kelvin.

Kraton™ 1112 is a polystyrene-polyisoprene linear block copolymer available from Shell Chemical Co., having approximately 40% diblock and 60% triblock, a styrene content of approximately 14%, and a midblock Tg of about 215 Kelvin.

Kraton™ RP-6411 is a polystyrene-polyisoprene linear block copolymer available from Shell Chemical Co., having approximately 64% diblock and 36% triblock, and a styrene content of approximately 22%.

Cariflex™ IR-309 is a polyisoprene elastomer available from Shell Chemical Co. having a number average molecular weight of 390,000, and a Tg of 215 Kelvin.

Wingtack™ 95 is a solid $C_5$ tackifying resin with a Tg of 323 Kelvin available from Goodyear Chemical Co.

Wingtack™ Plus is a solid $C_5$ tackifying resin with a Tg of 315 Kelvin available from Goodyear Chemical Co.

Escorez™ 1310 LC is a solid $C_5$ tackifying resin with a Tg of 313.5 Kelvin available from Exxon Chemical Corp.

Shellflex™ 371 is a naphthenic oil having about 10% aromatics as measured by clay-gel analysis having a Tg of 209 Kelvin and is available from Shell Chemical Co.

Zonarez™ A-25 is a liquid alpha-pinene tackifying resin with a Tg of 251 Kelvin available from Arizona Chemical Co.

Irganox™ 1076 is a hindered phenol antioxidant available from Ciba-Geigy.

The block copolymers used for fastening tapes 7 and 8 were admixtures of pure polystyrene-polyisoprene (S-I) diblock copolymer and polystyrene-polyisoprene-polystyrene (S-I-S) triblock copolymer (≧87% triblock) having the total percent diblock as indicated in Table I, the remaining fraction being essentially triblock.

Fastening tapes 1–9 were prepared by either solvent coating or hot melt coating each pressure-sensitive adhesive composition onto a polypropylene (polypropylene/polyethylene polymer blend for fastening tapes 5 & 6) film backing (backing thickness=approx. 4 mil). The pressure-sensitive adhesive compositions (in parts by weight) and adhesive coating thicknesses are given in Table I.

TABLE I

| | 1 | 2 | 3 | 4 | 5 | 6 | 7 | 8 | 9 |
|---|---|---|---|---|---|---|---|---|---|
| Kraton ™ 1107 | 33.5 | | | | | | | | |
| Kraton ™ 1111 | | 38.5 | | | | | | | |
| Kraton ™ 1112 | | | 52 | 52 | | | | | 29.6 |
| Kraton ™ RP-6411 | | | | | 50 | 50 | | | |
| 75/25 (S-I/S-I-S) 25% styrene | | | | | | | 61.7 | | |
| 77/23 (S-I/S-I-S) 25% styrene | | | | | | | | 58 | |
| Cariflex ™ IR-309 | | | | | | | | | 27.4 |
| Wingtack ™ 95 | | | | | | | 36.4 | 40.3 | |
| Wingtack ™ Plus | | 46.4 | 38 | 38 | 37.5 | 38.5 | | | 41.4 |
| Escorez ™ 1310 | 46.5 | | | | | | | | |
| Shellflex ™ 371 | | 15.1 | 10 | 10 | 12.5 | 10.5 | | | 1.6 |
| Zonarez ™ A-25 | 19 | | | | | | | | |
| Irganox ™ 1076 | 1 | 1 | 1 | 1 | 1 | 1 | 1.9 | 1.7 | 1 |
| | (100) | (101) | (101) | (101) | (101) | (100) | (100) | (100) | (101) |
| Adhesive thickness (microns) | 50 | 38 | 50 | 21 | 38 | 38 | 32 | 32 | 42 |
| Coating Method | Hot melt | Solvent | Hot melt | Hot melt | Hot melt | Solvent | Solvent | Solvent | Solvent |

EXAMPLES

Examples 1–27

Oil-filled polypropylene microporous films (15–35% oil) were prepared as described in U.S. Pat. Nos. 4,539,256 and 4,726,989 stretched by a ratio fo 1.6:1 in one direction. The oil was mineral oil (Amoco White mineral oil #31 available from Amoco Oil Co.). Fastening tapes 1–9 were tested against the microporous film samples for 1350 peel adhesion (using both tests described), shear adhesion, and for oil-contamination tolerance. The results are given in Table II. In Table II the microporous film samples are defined as A=35% oil, 1.7 mil caliper, B=30% oil, 1.7 mil caliper, C=25% oil, 1.3 mil caliper, D=20% oil, 1.2 mil caliper, and E=15% oil, 1.3 mil caliper. The effective pore size (measured using ASTM F-316-86) of film A was 0.2 microns, and the effective pore size of film C was 0.16 microns.

TABLE II

| Ex. | Porous Film | Fastening Tape | 135° Peel (2000 gm rolldown) | Shear | 135° Peel (loose) | 135° Peel (loose) w/oil |
|---|---|---|---|---|---|---|
| 1 | A | 1 | 433 | 10 | | |
| 2 | B | 1 | 595 | 7 | | |
| 3 | C | 1 | 871 | 47 | 156 | 76 |
| 4 | D | 1 | 1076 | 76 | | |
| 5 | E | 1 | 1474 | 184 | | |
| 6 | A | 2 | 589 | 1400+ | | |
| 7 | C | 2 | 506 | 1400+ | 297 | 127 |
| 8 | D | 2 | 575 | 1400+ | | |
| 9 | C | 3 | 480 | | 269 | 121 |
| 10 | A | 4 | 562 | 1320 | | |
| 11 | C | 4 | 425 | 1400+ | 99 | 60 |
| 12 | D | 4 | 431 | 1400+ | | |
| 13 | A | 5 | 766 | 1400+ | 157 | 95 |
| 14 | B | 5 | | | 234 | 145 |
| 15 | C | 5 | 720 | 1400+ | 355 | 175 |
| 16 | D | 5 | 728 | 1400+ scs | 523 | 278 |
| 17 | E | 5 | | | 590 | 341 |
| 18 | A | 6 | 887 | 1400+ | 193 | 113 |
| 19 | C | 6 | 731 | 1400+ | 416 | 213 |
| 20 | D | 6 | 750 | 1400+ | | |
| 21 | A | 7 | 1049 | 1400+ | 145 | 83 |
| 22 | C | 7 | 1040 | 1400+ | 306 | 166 |

TABLE II-continued

| Ex. | Porous Film | Fastening Tape | 135° Peel (2000 gm rolldown) | Shear | 135° Peel (loose) | 135° Peel (loose) w/oil |
|---|---|---|---|---|---|---|
| 23 | D | 7 | 1014 | 1400+ | | |
| 24 | A | 8 | 1049 | 1400+ | 166 | 101 |
| 25 | C | 8 | 1179 | 1400+ | 362 | 209 |
| 26 | D | 8 | 1105 | 1400+ scs | | |
| 27 | C | 9 | 555 | | 225 | 131 | scs = slight cohesive slippage

The oil-filled microporous films provided functional 135 degree peel performance against all tapes tested both when contaminated with oil and without oil. The shear performance of tape sample 1 was not acceptable except against the low oil-containing microporous films. Generally, superior peel performance was noted for the tapes having adhesives with a relatively high percent of elastomeric (polyisoprene) end blocks, as A-B diblock copolymers (tapes 3–8), with the possible exception of tape 4, which is attributable to the very low coating weight of the adhesive for that tape. The best peel performance was generally obtained for the lower percent oil-containing films, less than about 30 percent oil.

Examples 28 and 29

Fastening tapes 1 and 5 were tested against a particle-filled (calcium carbonate) 1.4 mil thick polyethylene microporous film. The microporous film had a Gurley Value of 900 sec/50 cc (measured by ASTM-D-726-58, method A). Results are given in Table III.

TABLE III

| Ex. | Tape | 135° Peel (2000 gm rolldown) | Shear | 135° Peel (loose) | 135° Peel (loose) w/oil |
|---|---|---|---|---|---|
| 28 | 1 | 482 | 92 | | |
| 29 | 5 | | | 603 | 204 |

This film is believed to contain a low amount of process oil. Peel performance for this film, when contaminated with oil, was excellent (Example 29).

Example 30 and 31

Fastening tapes 1–9 were tested against a particle-filled (barium sulfate) 0.75 mil thick polyethylene microporous film. The microporous film had a Gurley value of about 800 sec/50 cc (measured by ASTM-D-726-58, method A). Results are given in Table IV.

TABLE IV

| Ex. | Tape | 135° Peel (2000 gm rolldown) | Shear | 135° Peel (loose) | 135° Peel (loose) w/oil |
| --- | --- | --- | --- | --- | --- |
| 30 | 1 | 1808 | 764 | 315t | 80 |
| 31 | 2 | 836 | | | |
| 32 | 3 | 822 | | 237t | 234 |
| 33 | 4 | 503 | | | |
| 34 | 5 | 931 | | 367t | 316t st |
| 35 | 6 | 1001 | | 426t | 360 st |
| 36 | 9 | 894 | | 273t | 191 st | t = tore, st = stretched

This film was extremely thin and generally tore when not contaminated with oil and not reinforced (the 135° loose peel with 100 gm rolldown). However, the peel performance was generally excellent when contaminated with oil, with the possible exception of Tape 1 (which tape also displayed excessively high peels to this film when not contaminated).

Examples 37 and 38

A 1.7 mil oil-washed polypropylene microporous film (Example 37) and a 0.6 mil oil-washed polyethylene microporous film (Example 38) were prepared as described in U.S. Pat. Nos. 4,539,256 and 4,726,989. The Example 37 film originally had 35% mineral oil, and the Example 38 film originally had about 70% mineral oil, and were washed with trichloroethylene to remove the oil. Fastening tape 6 was tested against the washed films for 135° peel adhesion and for oil-contamination tolerance. Results are given in Table V. Example 38 tore.

TABLE V

| Ex. | Tape | 135° Peel (2000 gm rolldown) | 135° Peel (loose) | 135° Peel (loose) w/oil |
| --- | --- | --- | --- | --- |
| 37 | 6 | 1075 | 901 | 788 |
| 38 | 6 | 1326 | 49 t | 275 | t = tore

The oil contamination tolerance of these films was excellent.

Examples 39–42

Adhesive tapes having acrylate-based adhesives were tested against oil-filled polypropylene microporous films (35% and 25% oil, film samples A and C) for oil-contamination. The adhesive tape used for Examples 39 and 40 was Monta™ 391 (available from Monta of Germany) and the adhesive tape used for Examples 41 and 42 was Scotch™ Magic™ Tape (No. 11257, available from 3M Germany). Results are given in Table VI.

TABLE VI

| Ex. | Porous Film | 135° Peel (100 gm rolldown, loose) | 135° Peel (100 gm rolldown, loose) w/oil |
| --- | --- | --- | --- |
| 39 | A | 159 | 66 |
| 40 | C | 297 | 155 |
| 41 | A | 338 | 204 |
| 42 | C | 456 | 262 |

Examples 43 and 44

A natural rubber-based adhesive tape (Y-9377 available from 3M) was tested against oil-filled polypropylene microporous films (35% and 25% oil, film samples A and C) for oil-contamination tolerance. Results are given in Table VII.

TABLE VII

| Ex. | Porous Film | 135° Peel (100 gm rolldown, loose) | 135° Peel (100 gm rolldown, loose) w/oil |
| --- | --- | --- | --- |
| 43 | A | 373 | 225 |
| 44 | C | 522 | 256 |

Comparative Examples 45–48

Fastening tapes 1 and 5 were tested against smooth biaxially oriented polypropylene (BOPP) films, both with a low adhesion backsize (LAB) coating (Examples C45 and C46) and without an LAB (Examples C47 and C48). Results are given in Table VIII.

TABLE VIII

| Ex. | Tape | 135° Peel (2000 gm rolldown) | Shear | 135° Peel (100 gm rolldown, loose) | 135° Peel (100 gm rolldown, loose) w/oil |
| --- | --- | --- | --- | --- | --- |
| C45 | 1 | 168 | 823 | 46 | 9 |
| C46 | 5 | 574 | 1082 | 323 | 46 |
| C47 | 1 | 1975 | | 1284 | 28 |
| C48 | 5 | 1059 | 1400+ | 786 | 99 |

Tape 5 exhibited some oil tolerance, however, peel performance was vastly inferior to the peel performance of this tape against the oil-contaminated microporous films. Tape 1 did not perform well against the oil-contaminated non-porous films.

Comparative Examples 49–52

Fastening tapes 1, 5, 7 and 8 were tested against a conventional matte polyethylene film typical of those that are used for disposable diaper backsheets. Results are given in Table IX.

TABLE IX

| Ex. | Tape | 135° Peel (2000 gm rolldown) | Shear | 135° Peel (100 gm rolldown, loose) | 135° Peel (100 gm rolldown, loose) w/oil |
|---|---|---|---|---|---|
| C49 | 1 | 1352 | 400 | 435 | 12 |
| C50 | 5 | 587 | 865 | 307 | 39 |
| C51 | 7 |  |  | 707 | 165 |
| C52 | 8 |  |  | 776 | 232 |

Tapes 7 and 8 have the ability to adequately adhere to these polyethylene surfaces when contaminated with oil. However, the peels against the contaminated surface are less than one-third the peel performance against the non-contaminated surface. This limited oil-contamination tolerance is due to the properties of the adhesive used on tapes 7 and 8. Peel performance (contaminated vs. non-contaminated) was much more consistent for the tape 7 and 8 adhesives when adhered against the microporous films.

Examples 53–68

Examples 53–68 (Table X) are adhesive tapes prepared by solvent coating the adhesive composition onto a polypropylene film backing (4 mils). The adhesive thickness for these tapes was about 32 microns. The adhesives were all formed of elastomer with added solid tackifier.

The tapes were peel tested against a conventional matte polyethylene film such as is used for a disposable diaper backsheet. All these tapes exhibited some oil-contamination tolerance with the best peel performance to oil-contaminated surfaces obtained with adhesives with at least 60 weight percent, preferably 65–85 weight percent, S-I diblock copolymer in the elastomeric phase, having a percent styrene content of greater than 20 percent, preferably 22–26 percent, tackified with a solid $C_5$ tackifier or a beta-pinene resin.

Generally, oil contamination tolerance (a peel of at least 30 N/m) to a polyolefin surface, preferably polyethylene surfaces (with oil up to 0.12 mg/cm$^2$) was observed for polystyrene-polyisoprene-based adhesives where the elastomeric phase is greater than 40% diblock (the remainder being triblock or other multi-block copolymers); the elastomer has a percent styrene content of greater than 13 percent, preferably 15–30 percent; the solid tackifier compatible with the polyisoprene block is used in amounts ranging from 30 to 200 parts, preferably 40–120 parts, per 100 parts elastomer; and no more than 15 percent, preferably less than 10 percent, of the adhesive composition is a liquid resin or plasticizing oil. The solid tackifier is preferably a $C_5$ resin, a $C_9$ resin, a beta-pinene resin or a rosin ester.

Generally, these oil-tolerant adhesives are preferred for use with the oil-filled microporous film, oil-,contamination tolerant reinforcement strips as these adhesives exhibit high peels to the oil-contaminated surfaces, as well as not giving excessively high peels to the non-oil-contaminated oil-filled microporous films. These tapes also have the advantage of being able to adhere to oil-contaminated non-porous polyethylene film, which is useful if the porous reinforcement strip is missed.

These oil-tolerant adhesives adequately adhere to a polyethylene film, particularly if the polyethylene film is reinforced on the inner face opposite the outer face that the adhesive tape is attached to, such as by a film plastic strip or tape.

TABLE X

| Example | % Styrene | % S-I Diblock[1] | Parts[2] of solid resin | 135° Peel (100 gm rolldown, loose) | 135° Peel (100 gm rolldown, loose) w/oil |
|---|---|---|---|---|---|
| 53 | 15 | 40 | 70[3] | 498 | 116 |
| 54 | 15 | 40 | 70[4] | 577 | 142 |
| 55 | 15 | 55 | 70[4] | 567 | 143 |
| 56 | 17 | 65 | 75[5] | 618 | 158 |
| 57 | 17 | 79 | 70[4] | 806 | 176 |
| 58 | 17 | 79 | 70[6] | 718 | 167 |
| 59 | 17 | 79 | 70[7] | 656 | 154 |
| 60 | 17 | 80 | 49[5] | 699 | 175 |
| 61 | 19.6 | 65 | 75[5] | 724 | 175 |
| 62 | 19.6 | 80 | 49[5] | 710 | 189 |
| 63 | 22.6 | 65 | 75[5] | 777 | 194 |
| 64 | 25.6 | 65 | 75[5] | 786 | 187 |
| 65 | 22.6 | 80 | 49[5] | 832 | 180 |
| 66 | 25.6 | 80 | 49[5] | 784 | 204 |
| 67 | 22 | 70 | 70[3] | 898 | 172 |
| 68 | 22 | 80 | 70[6] | 825 | 177 |

[1]Remainder of elastomer is essentially S-I-S triblock
[2]Parts per 100 parts elastomer
[3]Wingtack ™ Plus (C5 resin from Goodyear Chemical Co.)
[4]Piccolyte ™ S-115 (beta-pinene based resin from Hercules Co.)
[5]Wingtack ™ 95 (C5 resin from Goodyear Chemical Co.)
[6]Arkon ™ P-115 (hydrogenated C9 resin from Arakawa Chemical)
[7]Floral ™ 85 (rosin ester available from Hercules Co.)

Example 69

Fastening tape 5 was tested against a porous heavily consolidated nonwoven polyethylene web (Tyvek™ 1422R) having an effective pore size of 9 microns. The web was embossed on one face. Both faces were tested for 135 degree peel using the loose peel test described above, both with and without oil contamination. The embossed face had peels of 131 gm/in and 72 gm/in for the non-oil-contaminated and oil-contaminated films, respectively. The smooth face had peel adhesions of 81 and 31 gm/in, respectively. These films displayed low peel values for the non-contaminated peel test which would indicate the presence of a surface treatment. However, the web did display oil-contamination tolerance properties.

Example 70

A 9.5 in×6 in sample of the 25% oil film (porous film C) with print was laminated onto an acrylate transfer adhesive and rolled over with a 4.5 lb roller. The transfer adhesive was made by pulling a 5-grains coating weight handspread of an RD-975 (available from 3M) acrylate adhesive on a release liner. A 9.5 in×2 in sample was then slit from the laminate, which was then laminated onto the front of a Pampers™ diaper. This sample was in turn rolled with a 4.5 lb roller to smooth out any wrinkles. The resulting diaper had a functional contamination-tolerant reinforcement strip.

We claim:

1. A disposable garment is provided with a thin liquid-impermeable sheet material and a pressure-sensitive adhesive closure system having at least one attachment region on the thin sheet material having an outer surface and a pressure-sensitive adhesive fastening tab having a free end to adhere to said at least one attachment region outer surface and a second opposite end permanently attached to a first edge region of the garment, said at least one attachment region provided adjacent a second edge region of said garment and having a polyolefin outer surface, said free end pressure-sensitive adhesive comprising:

100 parts of a block copolymer elastomer formed of polyisoprene and polystyrene blocks with at least 40 percent by weight polyisoprene-polystyrene di-block copolymer said elastomer having a total percent styrene content of at least 13 percent;

30 to 200 parts of an isoprene block compatible solid tackifier; and 0 to 15 percent by weight of a liquid resin or plasticizing oil, wherein when said free end pressure-sensitive adhesive is applied to said at least one attachment region, the pressure-sensitive adhesive fastening tab is capable of providing a 135 degree peel using a 100 gm rolldown of at least 30 N/m, with the attachment region having from 0 to 0.12 mg/cm$^2$ of mineral oil on its polyolefin outer face.

2. The disposable garment of claim 1 wherein said pressure-sensitive adhesive comprises 0–15 percent by weight plasticizing oil or liquid tackifier, and the solid tackifier is a $C_5$ resin, a $C_9$ resin, a beta-pinene resin or a rosin ester.

3. The disposable garment of claim 2 wherein said pressure-sensitive adhesive polyisoprene-polystyrene elastomer has a percent styrene content of 15–30 percent.

4. The disposable garment of claim 2 wherein said pressure-sensitive adhesive comprises at least 60 percent diblock copolymer having a percent styrene content of at least 20 percent, and the solid tackifier comprises a C5 tackifier or beta-pinene resin.

5. The disposable garment of claim 3 wherein the at least one attachment region outer surface comprises polyethylene.

6. The disposable garment of claim 5 wherein the said at least one attachment region comprises a reinforcement zone provided by a plastic strip or tape on the inner or outer face of the thin liquid-impermeable sheet material.

7. The disposable garment of claim 5 wherein the at least one attachment region is provided by a polyethylene plastic strip on the outer face of the thin liquid-impermeable sheet material.

8. The disposable garment of claim 4 wherein the elastomer contains 65–85 weight percent diblock having a percent styrene content of 22–26 percent, and the adhesive comprises 40 to 120 parts solid tackifier.

* * * * *

UNITED STATES PATENT AND TRADEMARK OFFICE
CERTIFICATE OF CORRECTION

PATENT NO.      : 6,191,055 B1
DATED           : February 20, 2001
INVENTOR(S)     : Boyer, Charles E. III It is certified that error appears in the above-identified patent and that said Letters Patent is hereby corrected as shown below:

Column 6,
Line 26, please delete "adhesions" and insert -- adhesion --.

Column 8,
Line 57, please delete "$\underline{\geq}87\%$" and insert -- $\geq 87\%$ --.

Column 9,
Line 30, please delete "fo" and insert -- of --.
Line 33, please delete "1350" and insert -- 135º --.

Column 13,
Line 55, please delete "oil-,contamination" and insert -- oil-contamination --.

Signed and Sealed this

Tenth Day of September, 2002

Attest:

Attesting Officer

JAMES E. ROGAN
*Director of the United States Patent and Trademark Office*